United States Patent [19]

Girard et al.

[11] Patent Number: 5,182,211
[45] Date of Patent: Jan. 26, 1993

[54] PLASMID VECTORS ENCODING A PROTEIN OF A PICORNAVIRUS

[75] Inventors: Marc Girard, Paris; Czeslaw Wychowski, Meurchin; Annette Martin, Paris, all of France

[73] Assignee: Institut Pasteur, Paris, France

[21] Appl. No.: 762,269

[22] Filed: Sep. 20, 1991

Related U.S. Application Data

[63] Continuation of Ser. No. 229,709, Aug. 8, 1988, abandoned.

[30] Foreign Application Priority Data

Aug. 7, 1987 [FR] France .................................. 87 11337

[51] Int. Cl.$^5$ ............................................. C12N 15/85
[52] U.S. Cl. .................................................. 435/320.1
[58] Field of Search ............... 435/255.1, 172.3, 320.1, 435/69.1, 69.3

[56] References Cited

U.S. PATENT DOCUMENTS 4,722,840  2/1988  Valenzuela et al. ................... 424/88

FOREIGN PATENT DOCUMENTS

83/02393  7/1983  PCT Int'l Appl. .
87/01386  3/1987  PCT Int'l Appl. .

OTHER PUBLICATIONS

Burke et al (1988) Nature 332:81–82.
de la Cruz (1988) J. Biol Chem 263:4318–4322.
CA 106:201712q (1986) Delpeyroux et al.
Delpeyroux et al (1986) Science 233:472–475.
Murray et al (1988) PNAS 85:3203–3207.
Burke et al (1989) G. Gen. Virol 70:2475–2479.
Yee, Jiing-Kuan (1987) Gene 53:97–104.
Kohara et al. J. Virol. vol. 53(3) pp. 786–792 Mar. 1985 "In Vitro Phenotypic Markers of a Poliovirus Recombinant Constructed from Infectious cDNA Clones of the Neurovirulent Mahoney Strain and the Attenuated Sabin 1 Strain".
Lai et al. J. Virol vol. 56(2) Nov. 1985 pp. 449–456 "Recombining between nonsegmented RNA Genomes of Murine Coronaviruses".
Semler et al. Proc. Natl Acad Sci vol. 83 pp. 1777–1781 Mar. 1986, "A chimaeric plasmid from cDNA clones of poliovirus and coxsackievirus produces a recombinant virus that is temperature-sensitive".
Stanway et al J. Virol vol. 57(3) Mar. 1986 "Construction of Poliovirus Intertypic Recombinants by Use of cDNA".
Martin, A. C. et al., Construction of a Chimeric Type 1/Type 2 Poliovirus by Genetic Recombination, Biol. Abst., vol. 85, Abstract No. 121461.

Primary Examiner—Richard A. Schwartz
Assistant Examiner—John Le Guyader
Attorney, Agent, or Firm—Finnegan, Henderson, Farabow, Garrett & Dunner

[57] ABSTRACT

The invention relates to an active principle of a vaccine, in which the characteristic epitope is incorporated in the capsid of a picornavirus, in particular of poliovirus, used as a vector. This active principle consists of a viable hybrid picornavirus containing an epitope characteristic of a vaccinating protein, and heterologous with respect to the proteins of this picornavirus, in place of one of its own immunogenic epitopes.

3 Claims, 5 Drawing Sheets

PLASMID VECTORS ENCODING A PROTEIN OF A PICORNAVIRUS

This application is a continuation of application Ser. No. 07/229,709, filed Aug. 8, 1988, now abandoned.

The poliovirus, which is known to be the agent of an infectious human disease, poliomyelitis or Heine-Medin disease, has been studied as a prototype of viruses of the Picornaviridae family. For the past few years the blossoming of genetic engineering has contributed to a better knowledge of this virus, and has made possible the molecular cloning of the viral RNA as cDNA, and the determination of the nucleotide structure of its genome (Kitamura et al. 1981; Racaniello and Baltimore, 1981, van der Werf et al., 1981). In addition, the possibility of inducing an infectious cycle in primate cells, using a plasmid carrying a complete copy of the viral genome, has contributed to the production of other vectors, whose specific infectivity it has been possible to increase (Semler et al., 1984, Kean et al., 1986). The study of other picornaviruses is also advancing rapidly. It will be recalled that the enteroviruses, of which types 1, 2 and 3 polioviruses constitute a subclass, belong to this class of viruses. They also include coxsackieviruses and echoviruses, rhinoviruses, cardioviruses, aphthoviruses and the virus of viral hepatitis A. The genomes of picornaviruses are RNAs whose size is generally of the order of 7500 nucleotides.

The work of Hogle et al., (1985), together with that of Rossmann (1985), shows that there are three major neutralization sites in picornaviruses: NImI on VP1, NImII on VP2 and VP1 and NImIII on VP3 and VP2 (NIm being an abbreviation of the term "neutralization antigen"). In type 1 poliovirus, an NImI site (amino acids 93-104, Wychowski et al., 1983), the C3 epitope of which is sequential, and NImII and NImIII sites, which determine confirmational sites at the surface of the virion, have been demonstrated.

In relation to the localization and identification of other immunogenic epitopes, reference may also be made, for polioviruses, to the work of E. A. Emini, A. Jameson, A. J. Lewis, G. R. Larsen and E. A. Wimmer, J. Virol. 43.997 (1982); R. Crainic et al., Infect. Immun. 41.1217 (1983); P. Minor et al., Nature (London) 301.674 (1983); P. Minor et al. J. Gen. Virol. 65.1159 (1985); M. Fergusson et al., Virology 143.505 (1985); D. C. Diamond et al. Science 229.1090 (1985); and D. M. A. Evans et al., Nature (London) vol 304, 459-462.

Similarly, reference may be made, for example, to the papers by Rossmann M. A. et al., (1985); Sherry B et al., J. Virol 57, 246-257 (1986) and Duechler et al. Proc. Natl. Acad. Sci. USA, vol. 84, pp. 2605-2609 (1987) in relation to the studies performed in order to localize and identify neutralizing epitopes carried by the rhinoviruses.

While most of the immunogenic epitopes identified to date are carried by the capsids of the viruses in question, at the surface of these capsids, there are others which have proved capable of inducing significant neutralizing responses, for example in rats and rabbits, without being at the surface. The peptide corresponding to the sequence of amino acid residues 113-121 of VP1, only a part of which is exposed (B. A. Jameson et al, in the work entitled "Vaccines" by R. Lerner et al, Eds. (Cold Spring Harbor Laboratory, Cold Spring Harbor N.Y. 1985) pp. 191-198), or peptides internal to viruses, for example those corresponding to the sequences of amino acid residues 61-80 and 180-201 of the poliovirus, have thus induced antibodies having substantial neutralizing properties.

The invention is based on the idea of using a picornavirus, capable of replicating in the cells of the host to be vaccinated against a specified pathogenic agent, as a vector carrying an immunogenic epitope which is heterologous with respect to this picornavirus and capable of inducing in the host the production of neutralizing antibodies against this pathogenic agent, the said epitope being incorporated in a protein of the picornavirus, in place of an immunogenic epitope which is neutralizing with respect to this picornavirus.

Preferred picornaviruses which are used as vectors are polioviruses, aphthoviruses and rhinoviruses.

In other words, the invention consequently relates to a viable hybrid picornavirus containing an epitope characteristic of a vaccinating protein, and heterologous with respect to the proteins of this picornavirus, in place of one of its own immunogenic epitopes. Preferably, the heterologous epitope is exposed at the surface of the capsid of the picornavirus. In particular, the epitope is then substituted for an endogenous immunogenic epitope of the picornavirus, normally exposed at the surface of the latter.

Generally speaking, it may also be stated that the heterologous epitope becomes incorporated by construction in the carrier protein which initially contained the endogenous immunogenic epitope of this picornavirus. Preferably, as has been seen, the heterologous epitope is exposed at the surface of the capsid. Nevertheless, the invention is not to be limited to this type of exposure. It relates equally to picornaviruses in which the heterologous epitope would be substituted for an internal natural immunogenic epitope, whose activity is nevertheless capable of being manifested in vivo.

In a preferred embodiment of the invention, the picornavirus which is a vector for the poliovirus capsid is a type 1 poliovirus in which the heterologous epitope is substituted for the C3 epitope normally exposed at the surface of the poliovirus capsid.

The invention also relates to the intermediate products involved in the construction of the viable hybrid picornaviruses, more especially the recombinant hybrid cDNAs comprising the whole or at least the portions of picornavirus cDNAs necessary for the production of a viable virus in a culture of competent cells in which the untransformed picornavirus is cultivable, on the one hand, and a heterologous nucleotide sequence, where appropriate synthetic, coding for a separate epitope, substituted in this cDNA for an endogenous or natural DNA sequence coding for an immunogenic amino acid sequence, on the other hand. Preferably, the heterologous sequence is substituted for an endogenous sequence which, in the unmodified picornavirus and taking into account the nature of the surrounding sequences, coded for an amino acid sequence exposed at the surface of the capsid of this picornavirus.

It relates more especially to recombinant plasmids in which the abovementioned hybrid cDNAs have been incorporated by construction, under the control of a promoter and of regulating elements permitting the autonomous replication of the corresponding recombinant picornaviruses in prokaryotic or eukaryotic organisms which are usable for the production of large amounts of picornavirus.

Accordingly, the invention relates more especially to plasmids carrying recombinant cDNAs derived from the cDNAs of polioviruses, aphthoviruses or rhinoviruses modified under the conditions described above by a polynucleotide coding for a heterologous immunogenic epitope, especially to plasmids which are usable for the transformation of prokaryotic or eukaryotic cellular organisms and permitting the autonomous replication and the production of the corresponding modified poliovirus, aphthovirus or rhinovirus.

The invention also relates to the recombinant RNAs containing the whole of the messenger RNA of the corresponding picornavirus, including the sequences coding for the VP0, VP3 and VP1 proteins, and comprising the substitution corresponding to that of the corresponding cDNA. This messenger RNA may be obtained either in vitro, or in previously transformed cell cultures, from a vector containing the cDNA of the corresponding picornavirus, under the control of a promoter and of suitable regulating elements.

It is quite remarkable that the modifications thereby introduced into viral proteins, more especially into those which normally possess immunogenic epitopes normally exposed at the surface of the capsids of the picornaviruses, in particular of polioviruses, may be carried out, in most cases, without impairing their viability. The invention consequently provides active principles which are usable for the formation of "live vaccines" or inactivated vaccines, from characteristic epitopes encoded by oligonucleotides which may have been produced synthetically. These vaccines can naturally also be produced from a natural nucleotide sequence, obtained by cleavage from the natural DNA or from a cDNA derived from the natural RNA coding for the protein which normally contains the amino acid sequence of the epitope.

The invention also relates to the vaccines themselves, obtained from the abovementioned viruses, in particular by inactivation of their virulence by classical methods, or live vaccines having attenuated virulence.

It may be noted that the methods applicable to the inactivation of poliovirus for the formation of vaccines against poliomyelitis are likewise applicable; for the record, and by way of example only, mention may be made of heat treatments, for example at between 50° and 60° C., and treatments with chemical agents such as formaldehyde or other suitable aldehydes, which may be used for obtaining these inactivated vaccines.

The major value of the vaccine according to the invention resides in the possibility of employing the fully dominated or dominable characteristics of picornaviruses, more especially of polioviruses, and of the vaccines against these picornaviruses, in particular of vaccines against poliomyelitis, for the manufacture of other vaccines. In addition, the heterologous epitopes of the new vaccines are presented to the body of the vaccinated host in a three-dimensional structure related to the natural immunogenic form of polioviruses.

The invention finally relates to a method for the production of the hybrid picornaviruses defined above, in which method, starting with a cDNA obtained from the viral RNA, and after a natural immunogenic epitope of the corresponding picornavirus has been localized beforehand, specific restriction sites are introduced (insofar as the latter were not already present) on each side of the natural immunogenic sequence to be replaced in the cDNA, the cDNA is cleaved at these specific sites by the corresponding restriction enzymes, a hybrid recombinant cDNA is reconstituted, formed from all the elements of the cDNA necessary for the subsequent replication of the virus which were previously associated with the sequence coding for the natural epitope, on the one hand, and of the sequence coding for the substituting immunogenic epitope in place of the sequence coding for the natural epitope, on the other hand, a sensitive cell culture is transfected with this recombinant DNA and finally the corresponding recombinant picornavirus is collected.

In relation to the information in the specific sites surrounding the sequence coding for the endogenous immunogenic epitope to be replaced, it is possible to employ any suitable method directed towards the introduction of a specific restriction site at a specified point of a nucleic acid. Advantageously, directed mutagenesis will be performed, for example as described in the example below.

In order to ensure that specific cleavage occurs at the desired points of the DNA to be treated, and in the absence of spurious cleavages in other regions of this DNA, the latter will preferably have been modified beforehand at these other points to eliminate the similar restriction 20 sites which could be present therein. This latter operation may be carried out by any suitable method enabling restriction sites to be modified, or alternatively by directed mutagenesis.

In the foregoing, only a limited substitution of the cDNA of the corresponding picornavirus has been mentioned. Those versed in the art will appreciate that it is also possible to envisage the production of more profoundly transformed hybrid viruses in order to meet the practical requirements. The abovementioned techniques make it possible, for example, to graft all or part of the complete sequence coding for the successive proteins, VP0, VP3 and VP1, of a rhinovirus or of HAV into the cDNA of a poliovirus, in place of the corresponding sequences coding for the proteins VP0, VP3 and VP1 of the poliovirus.

It is also necessary, in the latter case, to modify the specific cleavage sites in the cDNA of the rhinovirus or the HAV by directed mutagenesis, in order that the cleavages necessary to the subsequent production of the hybrid virus obtained between the proteins VP0 and VP3 on the one hand, and between the proteins VP3 and VP1 on the other hand, may be performed under the control of the sequence encoding for the specific protease which, in the natural poliovirus, cuts the glutamine-glycine bonds separating the abovementioned proteins.

This transformation consequently makes it possible to obtain a picornavirus derived from poliovirus, but provided with a rhinovirus or HAV capsid.

It will be clearly apparent to those versed in the art that constructions involving other combinations of different picornaviruses may be envisaged in the same manner, at the will of the constructor and as dictated by the maximum compatibility sought between the hybrid virus produced and the body of the host to be vaccinated.

Further characteristics of the invention will also become apparent in the course of the description which follows, of a method of construction of a hybrid recombinant DNA according to the invention derived from a type 1 poliovirus, with the support of FIGS. 1a to 5d, which illustrate diagrammatically the successive stages of this construction and the structures of the different plasmids employed.

I CONSTRUCTION OF THE MODIFIED SUBCLONING VECTOR pBR327

Plasmid pBR327 (SOBERON et al. 1980) (FIG. 1a) capable of replicating in *E. coli* bacteria, carrying the genes for resistance to ampicillin (Ap$^r$) and to tetracycline(Tc$^r$) and its origin of replication (ori), is chosen as the vector for performing the constructions. This vector is modified for the requirements of cloning in the following manner.

1. Replacement of the HindIII site (position 29) of this plasmid by an XhoI site The vector is opened at the HindIII site by the corresponding restriction enzyme (BOEHRINGER, conditions of use supplied by the firm), and the cohesive ends generated (40 μg DNA/ml) are filled in by treatment with KLENOW DNA polymerase (100 U/ml) in the presence of the 4 nucleotides (dNTP) (200 μM each) according to the protocol described by MANIATIS et al. (1982). The linearized DNA is dephosphorylated by treatment with calf intestinal alkaline phosphatase (2×0.02 units per μg of DNA) in a 50 mM Tris-HCl buffer pH 8.0, 10 mM MgCl$_2$, 0.1 mM EDTA, 1 mM ZnCl$_2$ (BOEHRINGER enzyme and protocol for use) twice for 30 minutes at 37° C., before ligation with a phosphorylated XhoI synthetic adapter (linker) (8 nucleotides, marketed by NEW ENGLAND BIOLABS). The ligation reaction is performed for 48 hours at +4° C. (or for 16 hours at +15° C.) in a solution 60 mM Tris-HCl pH 7.5, 1 mM EDTA, 10 mM MgCl$_2$, 10 mM DTT, 1 mM ATP, in the presence of one unit of T4 DNA ligase (BOEHRINGER) per μg of DNA, in a mole ratio of 100 (Linker/blunt-ended DNA). The ligation mixture is used for transforming *E. coli* HB101 bacteria (BOYER, ROULLAND-DUSSOIS, 1969) treated with calcium chloride (protocol: MANIATIS et al. 1982). The bacteria are then plated on agarose LB dishes containing ampicillin (100 μg/ml). The plasmids are extracted according to the technique described by BIRNBOIM and DOLY (1979) and screened for the purpose of isolating those containing the XhoI restriction site.

A plasmid pAM1 (FIG. 1b) possessing the XhoI restriction site in place of the HindIII restriction site is selected. This plasmid is prepared in large amounts after lysis of the bacteria with lysozyme/sodium dodecyl sulfate (GODSON and VAPNEK, 1973) and purification on a cesium chloride gradient. The plasmid DNA taken from the gradient is usable after successive volume-for-volume extractions with 1-butanol (3 times) and a 1:1 mixture of phenol saturated with TE (10 mM Tris-HCl pH 7.5, 1 mM EDTA) and chloroform/isoamyl alcohol (24:1). The extracted aqueous phase is precipitated by adding 2 volumes of 95% ethanol, and then centrifuged, and the pellet is taken up in a TE buffer.

2. Replacement of the EcoRV site (position 185) by a BglII site in the modified plasmid obtained In a similar manner, plasmid pAM1 is linearized at the EcoRV site, dephosphorylated and ligated with a phosphorylated BglII linker (8 nucleotides). Ampicillin-resistant clones are obtained after transformation of HB101 bacteria with the ligation mixture. The plasmids are prepared according to the technique described above, and analysed for the presence of the BglII restriction site. A plasmid pAM2 (FIG. 1c or FIG. 2a), possessing the XhoI and BglII restriction sites in place of the HindIII and EcoRV sites, respectively, is purified on a cesium chloride gradient.

II SUBCLONING OF THE XhoI-BglII FRAGMENT OF THE cDNA OF POLIOVIRUS TYPE 1 MAHONEY INTO THE VECTOR pAM2

The subcloning of a fragment comprising the first 5,601 nucleotides of the complementary DNA (cDNA) of poliovirus type 1 MAHONEY (out of 7,441 nucleotides) is carried out in such a way that the restriction sites to be generated in this fragment by directed mutagenesis are unique in the construction. The new restriction sites will thus be accessible by complete digestion with the corresponding restriction enzymes, so that the fragment included between these sites may be readily deleted and replaced by a substituting foreign sequence.

The "polio fragment" and the vector necessary for this subcloning are obtained as described below.

1. Polio fragment

Figure 1A:
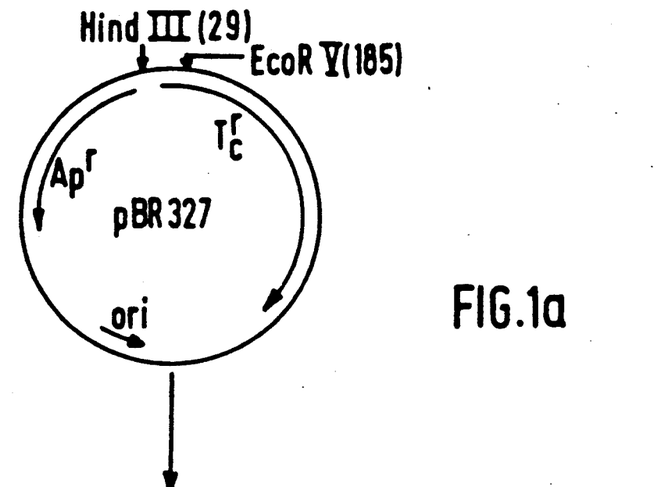
Figure 1B:
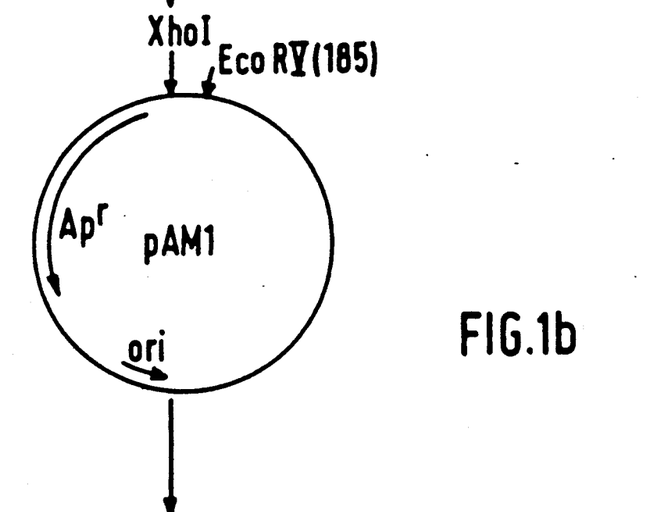
Figure 1C:
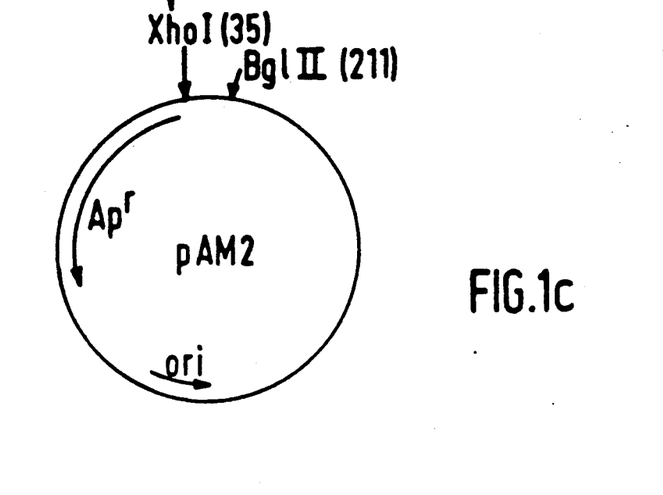
Figure 2A:
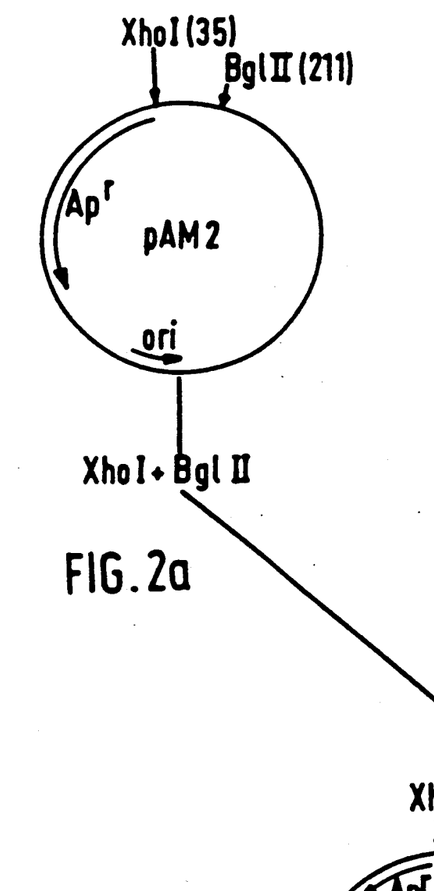
Figure 2B:
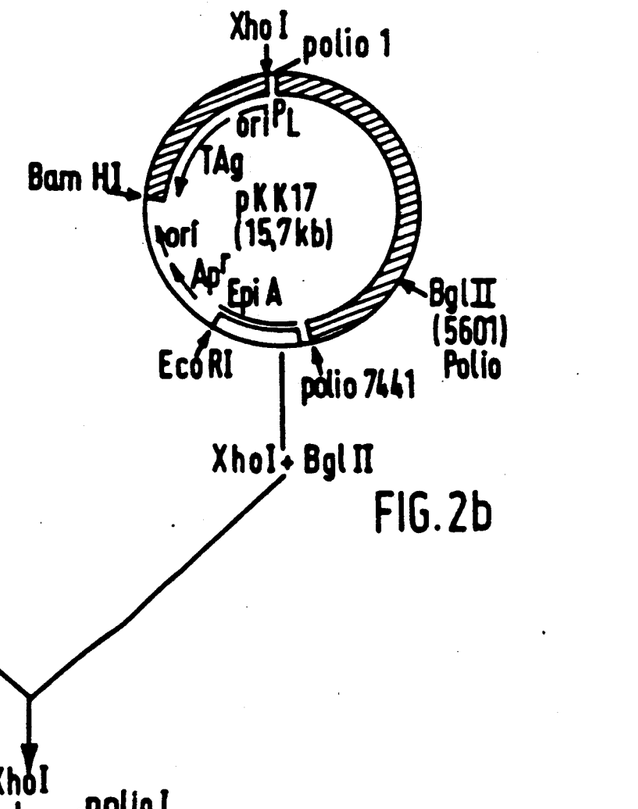
Figure 2C:
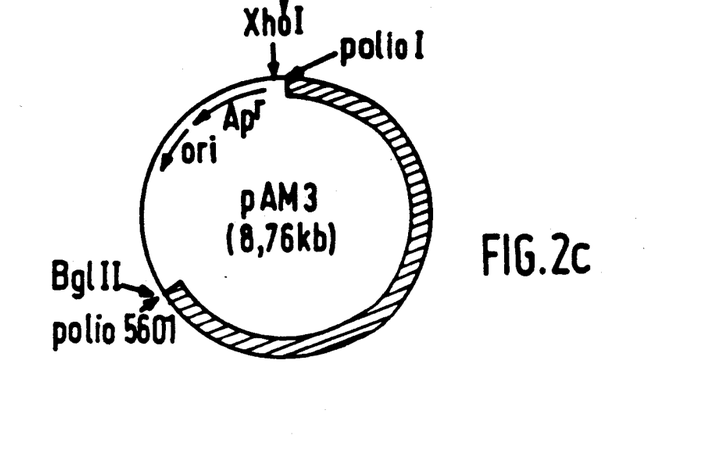

The XhoI-BglII restriction fragment containing the first 5,601 nucleotides of the polio cDNA (5638 base pairs) is derived from plasmid pKK17 (K. KEAN et al. 1986) (FIG. 2b). This plasmid contains the whole cDNA (represented by a hatched region) of the poliovirus cloned immediately after the SV40 late promoter PL present in the fragment (TAg) derived from SV40, as well as the elements necessary for its autonomous replication in monkey cells (SV40 origin of replication, transcription promoter, transcription enhancer sequence, functional T antigen). It also contains the bacterial origin of replication and the gene coding for resistance to ampicillin.

Plasmid pKK17 is digested completely with the restriction enzymes XhoI and BglII (BOEHRINGER) which correspond to single restriction sites in this plasmid. The 5,638-base pair (bp) fragment is isolated from a low-melting agarose gel (WIESLANDER, 1979), and purified by two extractions with phenol, an extraction with phenol/chloroform: isoamyl alcohol (IAA) mixture and two extractions with chloroform/isoamyl alcohol (IAA) mixture.

2. Vector

In parallel, plasmid pAM2 is digested completely (single sites) with the restriction enzymes XhoI and BglII. BglII-XhoI fragment (3,109 bp) containing the bacterial origin of replication and the gene for resistance to ampicillin is likewise isolated and purified from a low-melting agarose gel.

3. Subcloning

A ligation reaction of the two fragments (mol ratio insert/vector=2:1) is performed. HB101 bacteria are transformed with the ligation mixture. Ampicillin-resistant clones are obtained. The plasmid DNA is extracted and then analysed on the basis of the size of the fragments generated after digestion with the enzymes XhoI and BglII.

pAM3 (FIG. 2c or FIG. 3a), which possesses the sequence of the first 5,601 base pairs of the polio cDNA, is collected, and purified on a cesium chloride gradient.

III CREATION OF NEW RESTRICTION SITES IN THE SEQUENCE 1-5,601 OF POLIOVIRUS

The new restriction sites are created by the technique of directed mutagenesis by a synthetic oligonucleotide (MORINAGA et al. 1984), applied to a double-stranded plasmid, in this instance pAM3. To this end, it was chosen to create HpaI or EcoRV sites at position 2,756, and a HindIII site at position 2,786, in the poliovirus sequence. These two positions exactly frame the 93-103 loop of the capsid protein VP1, which corresponds to a type I neutralizing antigenic site of the poliovirus and is situated between two beta sheets. The restriction sites thereby generated will enable the nucleotide sequence coding for the amino acids on this loop to be deleted, and to be replaced by a heterologous sequence chosen on the basis of its antigenic role, with the objective of exposing this heterologous sequence at the surface of the virion.

The mutation of a single nucleotide in the poliovirus DNA can be sufficient to give rise to a new restriction site. The technique is used here to generate [by virtue of the corresponding pairs of synthetic oligonucleotides (see FIG. 3)] double mutants of poliovirus containing, as regards the first, HpaI and HindIII sites by the production of point mutations in positions 2,757 and 2,791, respectively, and, as regards the second, EcoRV and HindIII sites by mutations in positions 2,760 and 2,791, respectively.

These techniques are carried out using, in addition to the abovementioned plasmids, synthetic oligonucleotides. The latter each contain a point mutation compared with the nucleotide sequence of a portion of the single-stranded region to be obtained between positions 2,546 and 2.861, where it is desired to introduce the mutations.

3. The fragments I, IIa, IIb and IIc are individually purified by extraction with phenol, followed by precipitation with 95% ethanol. They are dissolved in TE buffer, 10 mM Tris-HCl pH 7.5, 1 mM EDTA. The fragments IIa, IIb and IIc are then reunited in the same solution.

4. The oligonucleotides were synthesized in an automatic synthesizer, and purified by high performance liquid chromatography (HPLC) and then by electrophoresis on acrylamide gel containing 7M urea. Finally, they were phosphorylated by treatment with T4 polynucleotide kinase ($2\times 1$ unit/$\mu$g DNA) in a 50 mM Tris-HCl buffer pH 9.0, 10 mM $MgCl_2$, 5 mM DTT, in the presence of 1 mM ATP, for $2\times 1$ hour at 37° C.

These oligonucleotides correspond to portions of the "wild-type polio sequence" whose structure follows. In particular, they contain a mutation of a nucleotide of the codon coding for the following amino acids:

93 for the oligonucleotide A,
104 for the oligonucleotide B, and
94 for the oligonucleotide C.

The above numbers correspond to the numbering of the amino acids of the protein VP1 which are encoded by the

```
         91        93                                              103
5'... G ACC GTG |GAT AAC| CCA GCT TCC ACC ACG AAT AAG GAT AAG |CTA| TTT
3... C TGG CAC |CTA TTG| GGT CGA AGG TGG TGC TTA TTC CTA TTC |GAT| AAA
       Thr Val |Asp Asn| Pro Ala Ser Thr Thr Asn Lys Asp Lys |Leu| Phe
          <------------>                                      <--------
                 HpaI                                          HindIII
            <--------------->
                 EcoRV 108
GCA GTG TGG 3'
CGT CAC ACC 5'
Ala Val Trp
-------->
 Hind III
``` above "polio fragment". Their lengths were chosen so as to frame the mutated nucleotide and to possess a minimum of homology with the other sequences of the wild-type MAHONEY poliovirus. The procedures are performed, in particular, under the conditions which follow.

Figure 3A:
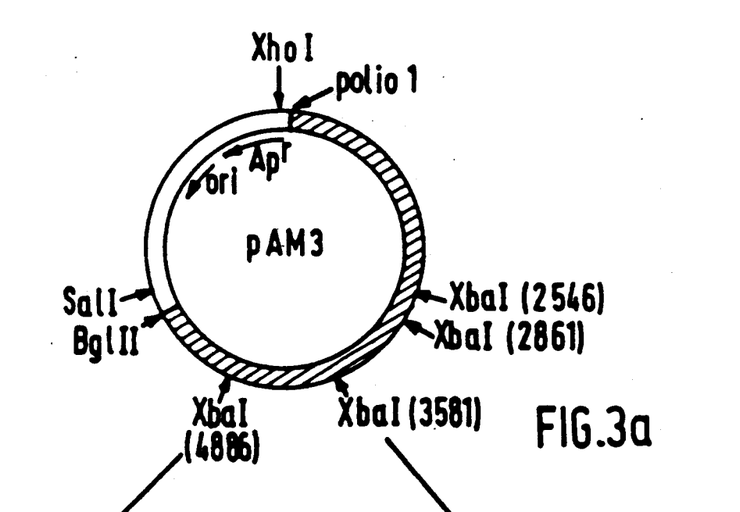
Figure 3B:
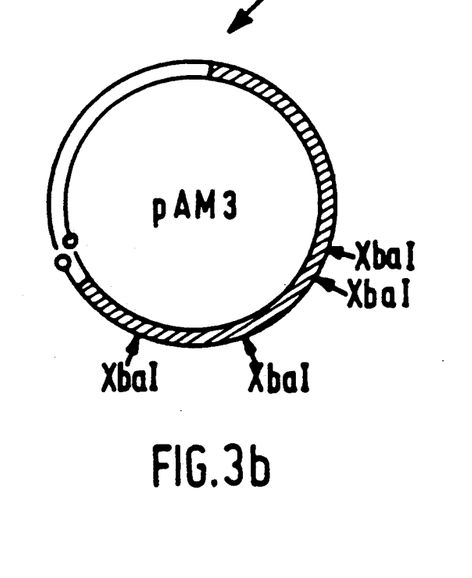
Figure 3C:
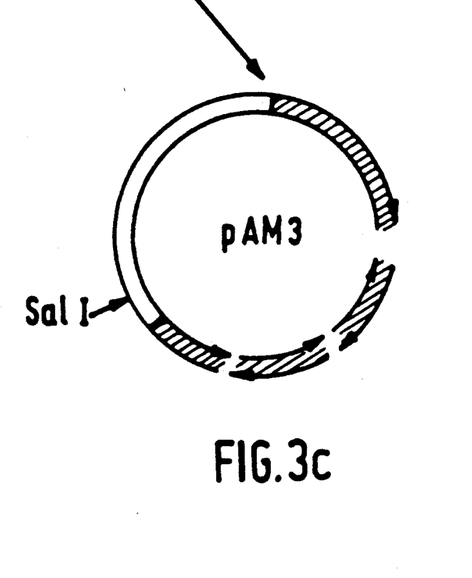

1. Plasmid pAM3 is digested with SalI (at position 651 of the pBR327 portion) to generate a linear fragment I (FIG. 3b).

2. Plasmid pAM3 is digested with XbaI, a site which is present at position 2,546, 2,861, 3,581 and 4,886 of the poliovirus cDNA fragment. Four fragments are hence generated, one of which (2,546-2,861) is removed after separation on the low-melting agarose gel. It will be noted that the fragment removed contained the nucleic acid sequence coding for the abovementioned 93-103 loop of the capsid protein VP1, as well as the nucleotides which surrounded it in what will be referred to later as the "wild-type polio sequence".

In contrast, the other 3 fragments are extracted. These possess respective sizes of 720 bp (fragment IIa), 1,305 bp (fragment IIb) and 6,405 bp (fragment IIc). After denaturation and hybridization with the pAM3 fragment digested with SalI, this will then enable a codons of the "wild-type polio sequence" below.

Under the lines identifying the codons of the "wild-type polio sequence" and the corresponding amino acids, an indication is shown of the relative positions of the synthetic oligonucleotides (arrows), the formulae of which follow, as a result of a point mutation in their respective structures (framed). These point mutations are illustrated by the use of outline letters, both to designate the substituting nucleotide resulting from this mutation, and to identify the change in nature of the amino acid encoded by the mutated codon.

Oligonucleotide A

```
HpaI 5' G ACC GTG G  T AAC CCA GC 3'
     3' C TGG CAC C  A TTG GGT CG 5'  synthetic
        91          93        95      oligonucleotide
        Thr Val     Asn Pro           (18-mer)
```

The HpaI site has been created by modifying the codon coding for the aspartate residue (position 93 of VP1) to a codon coding for valine (A 2,757>T).

Oligonucleotide B

```
HindIII 5' G GAT AAG CT  TTT GCA GTG TGG 3'
        3' C CTA TTC GA  AAA CGT CAC ACC 5' Oligonucleotide
           102     104           108        (22-mer)
           Asp Lys Leu Phe Ala Val Trp
```

The HindIII site results from a silent mutation (as regards the amino acid expressed) on the residue at VP1 position 104 (A 2,791>T).

Oligonucleotide C

```
EcoRV 5' CC GTG GAT A  C CCA GCT TCC 3'
      3' GG CAC CTA T  G GGT CGA AGG 5'  (20-mer)
            92           94      97
            Val Asp     Pro Ala Ser
```

The EcoRV site has been created by modifying the codon coding for an asparagine residue (position 94 of VP1) to a codon coding for an isoleucine (A 2,760>T).

The fragments I and II (0.03 pmol of each) are mixed in 10 μl of water, either with the oligonucleotides A and B, or with the oligonucleotides B and C, approximately 20 pmol of each of the oligonucleotides, to form either pairs of HpaI+HindIII sites, or pairs of EcoRV+HindIII sites, in the subsequent hybrid plasmids. 2 μl of 10-fold concentrated polymerase/ligase buffer (1M NaCl, 65 mM Tris-HCl pH 7.5, 80 mM MgCl$_2$, 10M B-mercaptoethanol) are added to these mixtures. The fragment mixture, contained in a sealed capillary, are denatured by incubation in a boiling water bath for 3 minutes, and the renaturation of the molecules is then carried out by slow cooling. Among the set of molecules formed, molecules are found in which a strand of the wild-type template is hybridized either with the oligonucleotide pairs A and B, or with the oligonucleotide pairs B and C.

Figure 4A:
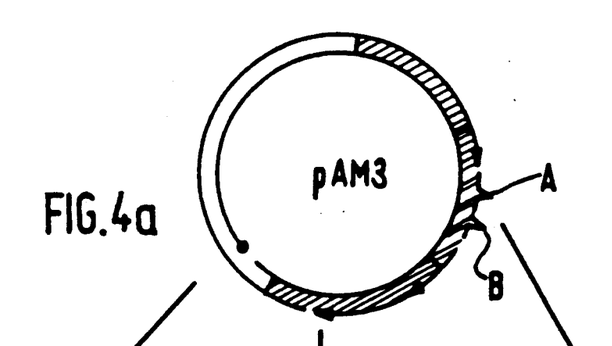
Figure 4B:
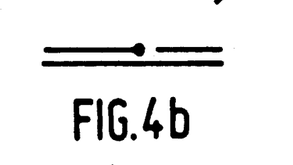
Figure 4C:
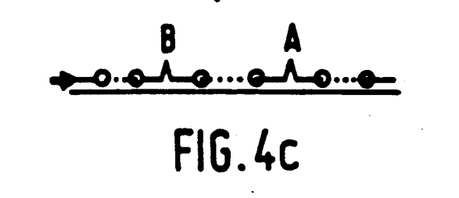
Figure 4D:
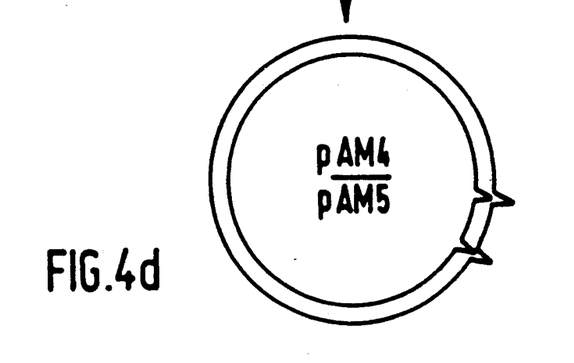
Figure 5A:
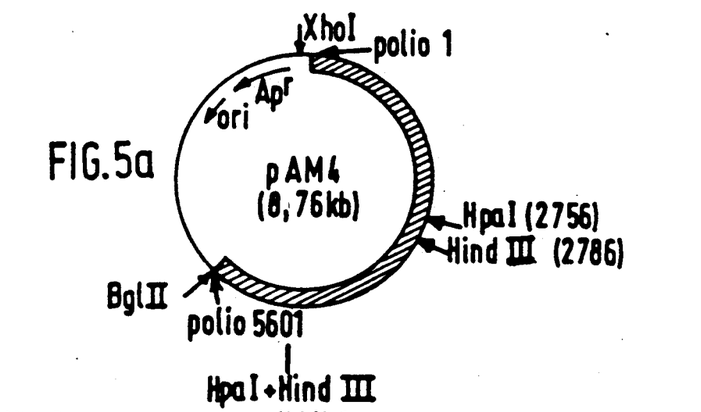
Figure 5B:
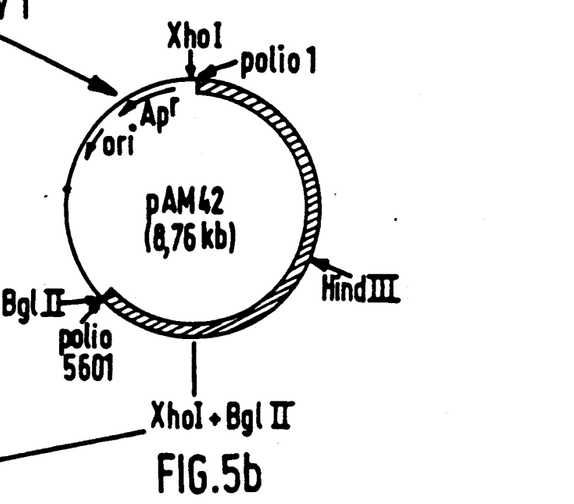
Figure 5C:
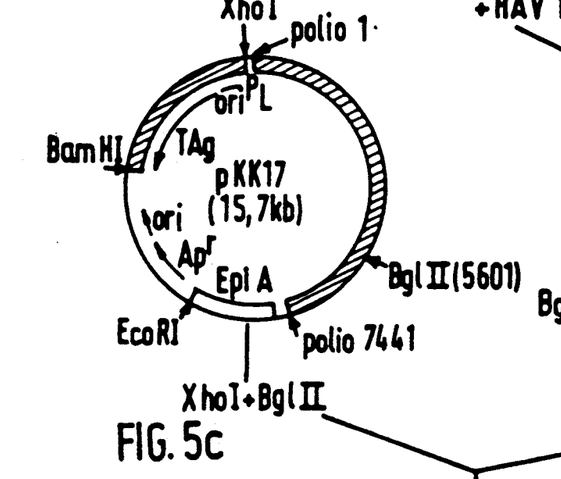
Figure 5D:
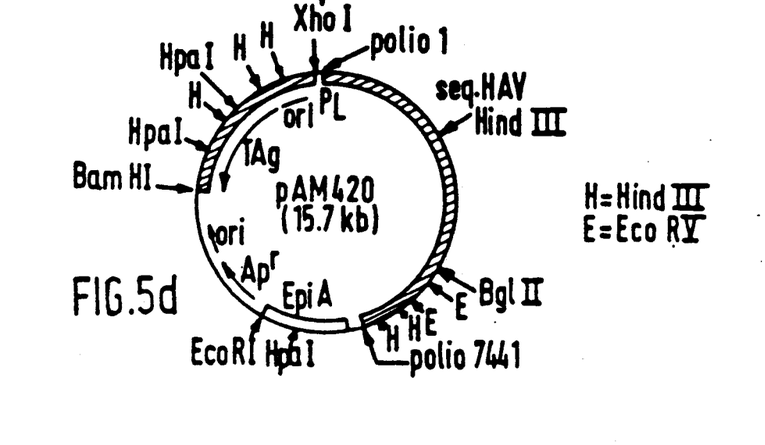

The product of these hybridations is illustrated in FIG. 4a, as regards, more especially, the first alternative above. It then only remains to fill in the still single-stranded portions of the template illustrated in FIG. 4b and 4c, which relate to fragments still containing these single-stranded portions, in which the insertions are represented by small angular projections.

To this end, the mixture is treated with KLENOW DNA polymerase [3 units+4 dNTP+T4 DNA ligase (3 units)] overnight at 12.5° C. in order that the single-stranded DNA is converted to a circular double-stranded DNA containing the mutations generated by the two oligonucleotides.

HB101 bacteria are transformed with the mixture; out of more than 1,000 ampicillin-resistant transformants used for retransforming HB101 bacteria in order to separate the mutant plasmids from the "wild-type plasmids" which may be present in the same transformant. The plasmids prepared according to the method of BIRNBOIM and DOLY are tested for the presence of the corresponding restriction sites, either HpaI and HindIII, or EcoRV and HindIII.

The plasmids selected (FIG. 4d) are:
pAM4: HpaI and HindIII sites
pAM5: EcoRV and HindIII sites.

The plasmids are prepared and purified on CsCl, and then sequenced to confirm the mutations. The sequencing is carried out according to ZAGURSKY's method, directly on the plasmid prepared according to the method of BIRNBOIM and DOLY or on cesium chloride.

IV CONSTRUCTION OF HYBRID PLASMIDS

The single HpaI and HindIII restriction sites in plasmid pAM4 (or EcoRV and HindIII of pAM5) enable the nucleotide sequence corresponding to amino acids 94 to 102 of the poliovirus VP1, that is to say to the C3 epitope, to be deleted, and to be replaced by any other sequence coding for a heterologous antigenic unit, for example of an enterovirus (type 2 or type 3 poliovirus or of hepatitis A) or of any other immunogenic heterologous epitope. Example of construction of a poliovirus plasmid (hepatitis A virus HAV) from pAM4 (FIG. 5a–5d)

Plasmid pAM4 (also shown in FIG. 4b) is digested with the restriction enzymes HpaI and HindIII, HpaI generating blunt ends and HindIII cohesive ends, and then dephosphorylated. The hepatitis A sequence is introduced in the form of two complementary oligonucleotides synthesized, purified and phosphorylated as described above, one of them being completed with an A and the other preceded by an AGCTT sequence (see below) in order to restore a HindIII site permitting ligation at cohesive ends with the vector. The two framed oligonucleotides, hybridized with one another as shown below, are then incorporated in the sequence of the poliovirus vector (in which the nucleotides and amino acids external to the HAV sequence are represented by outline letters), in particular by working as described below.

```
                                              HindIII
                                              ┌────┐
        72              VP1 HAV          81
5'     AAG CCT GGA GAG TCT AGA CAT ACA TCA GAT A│          3'

3'     TTC GGA CCT CTC AGA TCT GTA TGT AGT CTA TTC GA│      5'

Lys Pro Gly Glu Ser Arg His Thr Ser Asp
``` obtained for each construction, 600 transformants are screened by colony hybridization (according to GRUNSTEIN and HOGNESS 1975). The synthetic oligonucleotides, labeled with $^{32}$P by polynucleotide kinase, then serve as a hybridization probe for identifying the bacteria transformed by the mutated plasmids (hybridization carried out at 42° C, washings carried out at 53° C). About ten positive clones are selected and The ligation reaction is performed, in the presence of T4 DNA ligase, for 48 h at +4° C., between the vector bearing the deletion and the 2 hybridized oligonucleotides in a mole ratio of 1:20. HB 101 bacteria are transformed with the mixture and the transformant clones are analysed by colony hybridization with one of the two HAV oligonucleotides used as a $^{32}$P-labeled probe (hybridization at 37° C., washings at successive temperatures of 42° C. to 68° C.). The plasmids are extracted from the positive clones according to the method of Birnboim and Doly, and are tested for the presence of the HindIII site by digestion with the corresponding enzyme. A plasmid pAM42 (FIG. 5b) is selected. Its sequence in the insertion region is monitored by sequencing according to the method described.

The poliovirus sequence 1 to 5601, containing a heterologous sequence, is then replaced in plasmid pKK17 (shown again in FIG. 5c), so as to reconstitute a complete poliovirus cDNA. To this end, plasmid pAM42 is digested with the restriction enzymes XhoI and BglII, and the XhoI-BglII fragment (5641bp) containing the A plasmid pAM420 (FIG. 5d) is selected: it contains the whole of the poliovirus cDNA with the HAV insert, in a plasmid which is infectious for primate cells. It has subsequently given rise to the production of a hybrid poliovirus, hereinafter designated v420, under the conditions detailed later.

The plasmid is sequenced according to the technique described, in order to confirm the insertion sequences.

In the same manner, other sequences may be substituted for the antigenic site I of poliovirus type 1 Mahoney, for example:

the VP1 sequence 94 to 102 of poliovirus type 2 Lansing, by means of the following synthetic oligonucleotides:

```
                                              Hind III
                                           ┌─────────┐
          94          VP1  T2        102
5'    ┌─────────────────────────────────────┐
      │ AAT GAT GCT CCA ACA AAG CGT GCC AGT A │              3'
3'    │ TTA CTA CGA CGT TGT TTC GCA CGG TCA TTC GA │         5'
      └─────────────────────────────────────┘

Asn Asp Ala Pro Thr Lys Arg Ala Ser polio with          polio virus type 2 lansing sequence
amino acid 93
mutated
``` polio-HAV sequence is isolated and purified using a low-melting agarose gel. In parallel, plasmid pKK17 is also digested with XhoI and BglII, and the BglII-XhoI fragment (10028bp), containing the last 1840 base pairs of polio as well as the sequences necessary for the replication of the plasmid in bacteria and in primate cells, is isolated and purified in the same manner.

A ligation reaction is performed between the 2 fragments, and HB101 bacteria are transformed with the recombinant. The plasmids extracted from the transformant clones are analysed by double digestions with the restriction enzymes XhoI and HpaI and/or XhoI and HindIII, and screened on the basis of the size of the fragments obtained.

or the VP1 sequence 97 to 107 of HAV:

```
                                                     Hind III
                                                 ┌─────────┐
    93  97                VP1 HAV         107 103
5' GTG GTT │ACT TTT ACC TTC AAT TCA AAT AAT AAA GAG TAC AAG GTT TTT│ 3'
3' CAC CAA │TGA AAA TGG AAG TTA AGT TTA TTA TTT CTC ATG TTC GAA AAA│ 5'

Val Val  Thr Phe Thr Phe Asn Ser Asn Asn Lys Glu Tyr Lys Leu Phe polio with          HAV sequence
amino acid 93
mutated                                            polio
``` to form hybrid DNA sequences (in which the hybridized synthetic oligonucleotides are framed) containing the said VP1 sequences of HAV incorporated in the poliovirus cDNA.

The constructions made in plasmid pAM5 enable the mutation generated by the EcoRV restriction site to be removed, since it is present in the deleted sequence whereas, in plasmid pAM4, the mutation due to the HpaI site situated just upstream from the deleted sequence persists (valine instead of aspartate). A comparison of the two systems is of interest for studying the role of amino acid 93.

For example, the hybrid plasmid poliovirus/HAV 72-81 (also designated v520) characterized by the heterologous insertion below:

```
                                          Hind III
        72              YP1  HAY              81

5'    AAG CCT GGA GAG TCT AGA CAT ACA TCA GAT A         3'

3'    TTC GGA CCT CTC AGA TCT GTA TGT AGT CTA TTC GA    5'

Lys Pro Gly Glu Ser Arg His Thr Ser Asp
``` wild-type polio                HAV sequence has been constructed in pAM5.

V. STUDY IN ANIMAL CELLS

Type pAM420 hybrid plasmids are used for transfecting VERO or CV1 monkey kidney cells, or human cells (HeLa, Hep2, and the like), in the presence of DEAE dextran (McCutchan and Pagano, 1965), according to the method of Sompayrac and Danna (1981). The DNAs are prepared by the method of Birnboim and Doly or on a cesium chloride gradient.

$10^6$ CV1 or VERO cells are plated on 60 mm Petri dishes and incubated with 0.4 ml of a mixture containing 0.25 µg/ml of DNA in Dulbecco's modified Eagle's medium (DMEM) without serum, containing 50 mM Tris-HCl pH 7.5 and 500 µg/ml of DEAE-dextran. The incubation is performed at 37° C. in a $CO_2$ incubator for 2 hours. The cells are then washed with DMEM without serum, after which they are maintained in DMEM supplemented with 5% of fetal calf serum. After about 10 days, when the cytopathic effect (CPE) is total, the cells are then ruptured by 5 successive freezings/thawings in dry ice, and centrifuged for 30 min at 1500 rpm to remove the cell debris; the supernatant is used as a viral mini-stock.

The viral mini-stocks are titrated on 6-cup plates: the cups are seeded with $4 \times 10^5$ CV1 or VERO cells each, and then infected with 0.2 ml of the successive dilutions of the viral suspension in DMEM medium without serum, supplemented with 10 mM $MgCl_2$. Incubation is performed at 37° C. in a $CO_2$ incubator for 30 min. The viral suspension is then removed and the cells are covered with an agar containing DMEM with 2% of fetal calf serum. Two days after infection, the plates are stained with crystal violet: the agar is removed and the cell layer, pierced with lytic plaques, is stained with an aqueous solution containing 10% formaldehyde, 20% ethanol and 2 g/l of crystal violet. The lytic plaques are counted in the appropriate dilution. The titer of the viral suspension is expressed in plaque forming units (pfu)/ml.

The mini-stocks are used for manufacturing maxistocks of virus: to this end, $5 \times 10^6$ CV1 cells or $8 \times 10^6$ HEp2 cells (human epithelial cancer cells, in which poliovirus grows better) are plated on 100 mm Petri dishes and infected with the viral suspension at a multiplicity of 1 pfu/cell. Incubation is carried out at 37° C in a $CO_2$ incubator for 1 hour. The cells are then maintained in DMEM containing 2% of fetal calf serum. 22 hours later, when the CPE is total, the cells are treated as described for obtaining the mini-stock. The maxistock is also titrated.

The sequence of the viral RNA extracted from the virions composing this maxi-stock is monitored in respect of the insertion. Accordingly, from this maxi-stock, various analyses are carried out:

characterization of the viruses: reactions with polyclonal and/or monoclonal antibodies directed towards the vector poliovirus, and towards the antigen from which the heterologous epitope has been derived; where appropriate, the loss of the capacity to neutralize the picornavirus employed which was possessed by the monoclonal antibodies specific for the replaced sequence in this picornavirus, for example loss of the capacity of C3 monoclonal antibodies to neutralize the hybrid poliovirus or chimera derived from a type 1 poliovirus, as a result of the replacement of the C3 epitope by the heterologous epitope, is checked;

injection of purified hybrid viruses into rabbits, analysis of the sera obtained (ELISA, immunoblot, seroneutralization);

labeling and preparation of extracts of infected cells for analysis of the capsid proteins (in particular VP1) of the hybrid viruses on SDS-polyacrylamide gel (Laemmli, 1970).

if required, injection into rabbits of synthetic peptides corresponding to the sequences inserted into the poliovirus: analysis of the antibodies obtained: recognition and neutralization of the hybrid viruses.

Every time several epitopes capable of insertion into the picornavirus employed are available, those which display the best characteristics of heat resistance, and the best production yields compared with the unmodified picornavirus, are initially selected.

The hybrid picornaviruses selected can then be tested for their immunogenicity and their capacity to neutralize the pathogenic agents to which the epitopes inserted into the hybrid picornavirus correspond, in particular after injection into laboratory animals (mice, guinea-pigs, rabbits). The hybrid viruses or chimeras having, as far as possible, the stability and the yields of poliovirus in culture, and capable of inducing neutralizing antibodies at high titer in animals, not only against the poliovirus but also against the selected targets (for example HAV, HIV, rotavirus), are selected. These viruses are then tested for their capacity to induce a protection against a test infection by the virus in question in the appropriate animal systems (monkeys, chimpanzees, and the like).

In particular, for polioviruses modified by a sequence derived from hepatitis A virus (HAV), the immunogenicity of the new vaccinating principle may be tested as follows:

Approximately $10^8$ pfu of each clarified viral stock are mixed volume-for-volume with Freund's complete adjuvant (FCA) and injected into each rabbit of a batch of four rabbits (female - New Zealand white strain) intradermally (ID) by multipoint injector on the animal's back. A first booster is performed three weeks after the immunization, under the same conditions ($10^8$ pfu of virus injected ID in the presence of FCA). The sera derived from a bleeding collected two weeks after the booster are analysed by seroneutralization: the presence of antibodies neutralizing HAV, and also of antibodies neutralizing PV-1, is tested for.

In the methodology described above for the production of hybrid polioviruses or chimeras, the cDNA of the hybrids, cloned into the infectious plasmid pKK17 (described in part II-1), has been used directly to give rise to the corresponding viruses, by transfection of primate cells.

It is also possible to proceed via an in vitro transcription of the cDNAs, and to generate the corresponding viruses after transfection of the cells with RNAs of positive polarity obtained in vitro. The infectivity of these RNAs is superior than that of the cDNA clones, during transfections in primate cells.

For this second methodology, hybrid cDNAs are cloned, for example behind the phage T7 promoter (in a plasmid described by S. van der Werf et al., 1986) or the phage SP6 promoter of Salmonella (in a plasmid described by G. Kaplan et al., 1985). The cDNAs are transcribed in a cell-free system, using purified T7 RNA polymerase or using SP6 RNA polymerase, and capable of generating, in vitro, copies of infectious viral RNA of positive polarity. The very high specificity of T7 RNA polymerase for its own promoters, and its capacity to manufacture complete transcripts of long cDNAs, enable large amounts of RNA to be produced in this system. These RNAs serve as a template for the translation in the transfected cells.

Plasmid pT7PV1-5 described by S. van der Werf (1986), by virtue of its construction, enables RNAs (+) to be obtained, containing only two surplus G residues at the 5' end and 3 surplus residues downstream from the polyA at the 3' end. Removal of the long surplus sequences at the 5' and 3' ends of the RNAs produced from the initial constructions has enabled the infectivity of the RNAs to be increased from $10^3$ pfu/$\mu$g to $10^5$ pfu/$\mu$g (equivalent to approximately 5% of the infectivity of the viral RNAs extracted from the virions).

In addition, these methodologies may be applied generally to hybrid cDNAs over a larger portion of their genome. By the same system of a "cassette" framed by restriction sites which can be generated by directed mutagenesis, it is possible to delete the whole of the P1 portion of the poliovirus genome and replace it by a P1 region of another picornavirus, and generate hybrid viruses (with optional complementation by a system that can provide capsids of exogenous polioviruses, if necessary).

A number of neutralizing immunogenic peptides, capable of being incorporated as described above in the capsid proteins of a poliovirus, are also presented below and by way of non-limiting examples.

EXAMPLES OF IMMUNOGENIC SEQUENCES THAT HAVE BEEN INSERTED OR ARE CAPABLE OF BEING INSERTED IN AN APPROPRIATE CASSETTE VECTOR SUCH AS pAM4 or pAM5

For some of the polioviruses, viable hybrids have effectively been obtained; its designation is shown below in the form of a letter "v", followed by a number, as well as the designation of the plasmid employed in the construction of the intermediate cDNA. The corresponding hybrid sequences have been inserted in place of the C3 epitope of the poliovirus.

1/ Characteristic sequences of the virus of viral hepatitis A (HAV) coding for neutralizing immunogenic peptides [J. COHEN et al (1986) J. VIROL 61, 50–59], in particular, the sequences corresponding to:

the HAV VP1 region 102-110 (v545; pAM5)

102                                   110
5' Ser Asn Asn Lys Glu Tyr Thr Phe Pro 3'

5' TCA AAT AAT AAA GAG TAC ACA TTT CCA A 3'
(28-mer)

3' AGT TTA TTA TTT CTC ATG TGT AAA GGT TTCGA 5'
(32-mer)

the HAV VP1 region 102-115

102                                   110
5' Ser Asn Asn Lys Glu Tyr Thr Phe Pro Ile Thr Leu Ser

115
Ser 3'

5' TCA AAT AAT AAA GAG TAC ACA TTT CCA ATA ACC TTG TCT

TCG A 3' (43-mer)

3' AGT TTA TTA TTT CTC ATG TGT AAA GGT TAT TGG AAC AGA

AGC TTCGA (47-mer)

the HAV VP1 region 99-106

Thr Phe Asn Ser Asn Asn Lys Glu surrounded by the residues Asp(93)-Asn(94), on the one hand, and Lys(103), on the other hand, of the poliovirus VP1 the HAV VP3 region 67-76 (v564; pAM5)

Asn Ala Ser Asp Ser Val Gly Gln Glu Ile surrounded by the residues Asp(93) and Lys(103) of the poliovirus VP1

2/ Characteristic sequences of the hepatitis B virus coding for neutralizing immunogenic peptides of this virus, these peptides corresponding to the region 120-145 of the reading frame coding for pre-S
(N-terminal region of the middle protein: 33 and 36kD).

```
              120                            130
5' Met Gln Trp Asn Ser Thr Ala Phe His Gln Thr Leu

140
    Gln Asp Pro Arg Val Arg Gly Leu Tyr Leu Pro Ala

Gly Gly 3'
``` ref. A. R. NEURATH, S. B. H. KENT, N. STRICK (1984). Science, 224, 392–394.

the pre-S region 12-32

```
     12                          20
5' Met Gly Thr Asn Leu Ser Val Pro Asn Pro Leu Gly 30   32
    Phe Phe Pro Asp His Gln Leu Asp Pro 3'
``` ref. A. R. NEURATH, S. B. H. KENT, N. STRICK, P. TAYLOR, C. E. STEVENS, Nature 315, 154-156 (1985)

the S region 139-147

```
           139                         147
     5' Cys Thr Lys Pro Thr Asp Gly Asn Cys 3'
``` ref. BHATNAGAR et al. (1982), PNAS 79, 4400–4404. THANAVALA et al. (1986), J. Exp. Med; 164, 227–236

3/ Sequences coding for immunogenic peptides of herpes simplex type 1 virus, in particular region 8-23 of the mature glycoprotein D
(residues 33 to 48 of the predicted sequence of gD1).

```
         8              10
5' Ser Leu Lys Met Ala Asp Pro Asn Arg Phe Arg Gly 20      23
    Lys Asp Leu Pro 3'
``` ref. COHEN et al. (1984), J. Virol. 49, 102, 108.

region 340-356 of the glycoprotein D
(residues 365 to 381 of the predicted sequence).

```
         340                              350
5' His Arg Arg Thr Arg Lys Ala Pro Lys Arg Ile Arg

356
    Leu Pro His Ile Arg 3'
``` ref. EISENBERG et al. (1985), J. Virol. 53, 634–644 or region encoded by the HSV-1 glycoprotein D sequence:

R. J. WATSON, J. H. WEIS, J. S. SALSTROM, L. W. ENQUIST. (1982), Science 218, 381-384.

4/ Sequences coding for an immunodominant surface antigen of the circumsporozoite of *Plasmodium falciparum*, the agent of malaria, in particular an antigenic unit present on the CS protein (circumsporozoite protein -412 amino acids and containing 41 repetitions of a tetrapeptide at a central position of the protein). The antigen unit which is usable then consists of a number, for example 4, repetitions of the tetrapeptide - Pro Asn Ala Asn - ref.

V. ENEA et al. (1984) - Science 225, 628–630
J. B. DAME et al. (1985) - Vaccines 85 - Cold Spring Harbor Laboratory (7–11)
ref. sequence protein CS: J. B. DAME et al. (1984) Science 225, 593–599.

5/ Epitope of the influenza virus containing the residues 138-164 of the hemagglutinin ref: M. SHAPIRA, M. JIBSON, G. MULLER, R. ARNON (1984) PNAS 81, 2461-2465.

6/ Characteristic epitopes of the envelope glycoprotein of HIV 1 and HIV 2, for example epitopes which are important for seroneutralization, localized in the gp120, as defined, respectively, by the Bolognesi and Putney groups (type-specific epitope) and by the group of Ho and co-workers (group-specific epitope) or by Matsuhito et al, J. Virol. 1988, 62, 2107–2114; or alternatively broadspecificity neutralization epitopes as identified in the gp41, the latter furthermore carrying the hydrophobic sequence necessary for the fusion of the envelope of the virus with the cell membrane (Robin Weiss).

In particular, it is possible to employ the Bolognesi-Putney epitope (Putney et al, Science, 1986, 234, 1392–1395) (traditionally described in the form of a loop consisting of amino acids 301 to 336 of the gp120):

```
NH2—C—T—R—P—N—N—N—T—R—K—S—I—R—I—Q—R—G
    |            307           310             \
    S                                            P
    |                                            |
    S                                            G
    |                                           /
COOH—C—H—A—Q—R—M—N—G—I—K—G—I—T—V—F—A—R
                330                       320
``` or portions of the loop corresponding to the sequences N T R K S I R I Q R G P G R [possibly sufficient for inducing neutralizing antibodies specific for the type IIIB variant (LAV-1)], or the sequence K G P G R V I, capable of inducing antibodies neutralizing the RF variant.

It is also possible to make use of the second epitope of the gp120 (amino acid sequence 254 to 271 of Ho et al, 1988, Science 239, 1021):

C T H G I R P V V S T Q L L L N G S which induces antibodies neutralizing (at various levels) all the African, European and American variants tested; or of a portion of this epitope: G I R P V V S T Q L. These epitopes are especially advantageous to include in a vaccine, since they should enable antibodies having a broad neutralization spectrum to be induced.

By way of other usable epitopes, mention may be made of the epitope of the gp41 corresponding to amino acids 735 to 752, namely:

G I E E E G G E R D R D R S I R L V N G
740                                  750 or the epitone (LASKY et al) which appears to be involved in the recognition of the CD4 receptor (amino acids 404 to 425):

I K Q I I N M W Q K V G K A M Y A P P I S G
410                                    420

7/ Epitope of VP3 and VP7 polypeptide chains for protection against rotavirus;

such as the epitopes identified recently by Mackow, Harry Greenerg et al (Proc. Natl. Acad. Sci., 1988, 85, 645–649), in particular:

Special mention may be made of the epitopes carried by VP3, the amino acid sequences 87 to 89:

L L A P T A A G V V V E G T
         90

148 to 150:

D V V K T T Q N G S Y S Q Y G P
             150 and 388 to 393:

G D Y S F A L P V G Q W P
              390

The latter epitope appears to be especially advantageous, since the neutralizing antibodies which correspond to it show a substantial cross reactivity with several serotypes of rotavirus.

Other neutralization epitopes present on VP7 may be used, especially those coinciding with the regions of amino acids 87 to 101 and 208 to 221 (Taniguchi, Channock et al, Virol., 1988, 62, 1870–1874), in particular those carrying sequences:

T E A S T Q I N D G D W K D S L S Q and

G C Q T T N V D S F E M V A E N.

8/ Epitopes of the rabies virus glycoprotein.

9/ Epitopes of the cholera antigen (French Patent 83/13,828, published under No. 2,551,088), and the like.

It is naturally self-evident that any other epitope may be employed for the production of vaccines, preferably of live vaccine, using a picornavirus having attenuated virulence by way of a carrier vector (for example a SABIN strain). These vaccines will be intended for man or for animals, depending on the nature of the chosen epitope and of the chosen vector. It will also be immediately apparent to those versed in the art that the picornavirus used by way of a vector may also be a virulent virus, in which case use will be made of the recombinant obtained in order to manufacture an inactivated vaccine. Finally, it is a matter for the clinician to determine the doses and the protocol for administration of the chosen vaccine, according to the mammal for which it is intended.

For the purpose of information, references for the papers by the authors to whom reference has been made above are also given below.

Finally, it is self-evident that the invention is not limited to only the C3 epitope (NIM I site), but that similar constructions may be undertaken at the NIM II (VP2) and NIM III (VP3) sites. In particular, it is possible to replace 2 of the 3, or even all 3, neutralization sites of the vector picornavirus (for example poliovirus 1) by the 2 or 3 corresponding neutralization epitopes originating from another picornavirus (for example HAV).

In the case already mentioned above, where, for example, the rhinovirus capsid is substituted for the poliovirus capsid, or vice versa, it is naturally understood that this substituting capsid can in turn be locally substituted by an epitope which is heterologous with respect to this capsid, this being as a replacement for the natural epitope of this capsid, which, in the picornavirus from which it originates, is at the surface of the said capsid.

It is finally self-evident that the term "epitope" as has been used in the context of the present text, is not to be interpreted in a restrictive manner. In particular, the term "epitope" is not limited to only the sequence of amino acids to which is attributed the capacity for inducing in vivo neutralizing antibodies against the antigen from which this epitope has been taken. The term should be understood to encompass, where appropriate, shorter or longer amino acid sequences which, normally, surround the epitope (in the restricted sense of the term) in the antigen from which it has been taken. It has been seen that these sequences could even, in the case of picornaviruses, go as far as including all the capsid proteins of the particular picornavirus from which the substituting antigen has been taken.

It is thus also possible to perform the transfer of substitutions carried out in the cDNA of a wild-type strain (Mahoney) into the cDNA of a Sabin strain. The invention hence enables orally usable live chimeral vaccines to be developed. This may be envisaged, in particular, for the production of vaccines against hepatitis A and diarrhea caused by rotavirus. The direct subcloning, which has become possible, of the fragment of plasmid pAM5 substituted in Sabin cDNA should make it possible to satisfy this source of concern.

It is, moreover, self-evident that all the operations which have been described in the foregoing apply in the same way to a cDNA derived from a type I Sabin strain itself, for example by the substitution, in this cDNA, of an oligonucleotide containing the sequence coding for the chosen heterologous epitope, for the endogenous sequence coding for the peptide corresponding essentially to the C3 epitope of the protein VP1 of Mahoney strain, in this instance:

His Val Val Gln His

Arg Ser Arg Ser Glu Ser Ser Ile Glu Ser

Phe Phe Ala Arg Gly Ala Cys Val Ala Ile

Ile Thr Val Asp Asn Ser Ala Ser Lys Thr

Asn Lys Asp Lys Leu Phe Thr

REFERENCES

Birnboim, H. C. and Doly, J. (1979) Nucl. Acids Res., 7, 1513–1522

Boyer, H. W. and Roulland-Dussois, D. (1969) J. Mol. Biol., 41, 459–472

Emini, E. A., Hughes, J. V., Perlow, D. S. and Boger, J. (1985) J. Virol., 55, 836–839

Godson, G. N. and Vaepnek D. (1973) Biochim. Biophys. Acta, 299, 516–520

Grunstein, M. and Hogness, D. S. (1975) Proc. Natl. Acad. Sci. USA, 72 3961–3965

Hogle, J. M., Chow, M. and Filman, D. J. (1985) Science, 229, 1358–1365

Kaplan, G., Lubinski, J., Dasgupta, A. and Racaniello, V. R. (1985) Proc. Natl. Acad. Sci. USA, 82, 8424–8428

Kean, K. M., Wychowski, C., Kopecka, H., and Girard, M. (1986) J. Virol., 59, 490–493

Kitamura, N., Semler, B. L., Rothberg, P. G., Larsen, G. R., Adler, C. J., Dorner, A. J., Emini, E. A., Hanecak, R., Lee, J. J. van der Werf, S., Anderson, C. W. and Wimmer, E. (1981) Nature, 291, 547–553

Laemmli, U. K. (1970) Nature, 680–685

Maniatis, T., Fritsch, E. F., Sambrook, J. (1982) Molecular Cloning. A Laboratory Manual. Cold Spring Harbor Laboratory Press, N.Y.

McCutchan, J. M. and Pagano, J. S. (1968) J. Natl. Cancer Inst., 41, 351–356

Morinaga, Y., Franceschini, T., Inouye, S. and Inouye, M. (1984) Biotechnology, 636–639

Racaniello, V. R. and Baltimore, D. (1981) Proc. Natl. Acad. Sci. USA, 78, 4887–4891

Rossmann, M. A., Arnold, E., Erickson, J. W., Frankenberger, E. A., Griffith, J. P., Hecht, H. J., Johnson, J. E., Kamer, G., Luo, M., Mosser, A. G., Rueckert, R. R., Sherry, B. and Vriend, G. (1985) Nature, 317, 145–153

Semler, B. L., Dorner, A. J., and Wimmer, E. (1984) Nucl. Acids Res., 12, 5123–5141

Soberon, X., Covarrubias, L. and Bolivar, F. (1980) Gene, 9, 287–305

Sompayrac, L. M. and Danna, K. (1981) Proc. Natl. Acad. Sci. USA, 78, 7575–7578 van der Werf, S., Bregegere, F., Kopecka, H., Kitamura, N., Rothberg, P. G., Kourilsky, P., Wimmer, E. and Girard, M. (1981) Proc. Natl. Acad. Sci. USA, 78, 5983–5987 van der Werf. S., Bradley, J. Wimmer, E., Studier, F. W., and Dunn, J. J. (1986) Proc. Natl. Acad. Sci. USA, 83, 2330–2334

Wieslander, L. (1979) Anal. Biochem., 98, 305–309

Wychowski, C., van der Werf, S., Siffert, O., Crainic, R., Bruneau, P., and Girard, M. (1983) The EMBO J, 2, 2019–2024

Zagursky, R. J., Baumeister, K., Lomax, N., and Berman, M. L. (1985) Gene Analysis Techniques, 2, 89–94

We claim:
1. Plasmid pAM4.
2. Plasmid pAM5.
3. Plasmid pAM420.

* * * * *